United States Patent
Drummond et al.

(10) Patent No.: US 6,628,743 B1
(45) Date of Patent: Sep. 30, 2003

(54) METHOD AND APPARATUS FOR ACQUIRING AND ANALYZING CARDIAC DATA FROM A PATIENT

(75) Inventors: Danielle Drummond, Wauwatosa, WI (US); Kristin Leigh Carreau, Kenosha, WI (US); Tin-Su Pan, Brookfield, WI (US); Shankara B. Reddy, Cedarburg, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/065,859

(22) Filed: Nov. 26, 2002

(51) Int. Cl.$^7$ ................................................ A61B 6/03
(52) U.S. Cl. ............................ 378/8; 378/15; 378/901
(58) Field of Search ......................... 378/4, 8, 15, 98.12, 378/901

(56) References Cited

U.S. PATENT DOCUMENTS

| | | | |
|---|---|---|---|
| 6,185,447 B1 | * 2/2001 | Alley et al. | 600/420 |
| 6,373,920 B1 | 4/2002 | Hsieh | 378/98.11 |
| 6,438,403 B1 | 8/2002 | Cline et al. | 600/410 |
| 6,447,453 B1 | 9/2002 | Roundhill et al. | 600/443 |
| 6,493,571 B1 | * 12/2002 | Bis et al. | 600/420 |
| 6,496,560 B1 | * 12/2002 | Lin et al. | 378/62 |

OTHER PUBLICATIONS

Antman, Elliott M. et al., "Abciximab Facilitates the Rate and Extent of Thrombolysis– Results of the Thrombolysis in Myocardial Infarction (TIMI) 14 Trial", Circulation, Jun. 1, 1999, pp. 2720–2732.

Keegan, Jennifer et al., "Interleaved Spiral Cine Coronary Artery Velocity Mapping", Magnetic Resonance in Medicine, vol. 43, 2000, pp. 787–792.

Medina, R. et al., "Reconstruction of the left ventricle shape from two angiographic views: a fuzzy and evolutionary approach", Comupters in Cardiology, Hannover, Germany, Sep. 1999, pp. 1–2.

(List continued on next page.)

Primary Examiner—David V. Bruce
(74) Attorney, Agent, or Firm—Cantor Colburn LLP

(57) ABSTRACT

A method for acquiring and analyzing cardiac data of a patient includes acquiring a first volume of cardiac data from a medical scanner, processing the first volume of cardiac data for image reconstruction and visualization, acquiring a subsequent plurality of volumes of cardiac data from the medical scanner, processing the subsequent plurality of volumes of cardiac data for image reconstruction and visualization, and reconstructing and visualizing the first and subsequent plurality of image sets from the acquired first and the subsequent plurality of volumes of cardiac data, respectively. The method for acquiring and analyzing cardiac data of a patient includes processing the cardiac images for detection and diagnosis of heart diseases.

26 Claims, 11 Drawing Sheets

OTHER PUBLICATIONS

Miles, K.A., "Measurement of tissue perfusion by dynamic computed tomography", The British Journal of Radiology, vol. 64, No. 761, pp. 409–412.

Mochizuki, Teruhito et al., "Demonstration of Acute Myocardial Infarction by Subsecnd Spiral Computed Tomography–Early Defect and Delayed Enhancement", Circuation, 99: 1999, pp. 2058–2059.

Rumberger, John A. et al., "Use of Ultrafast Computed Tomography to Quantitate Regional Myocardial Perfusion: A Preliminary Report", Journal of the American College of Cardiology, vol. 9, No. 1, Jan. 1987, pp. 59–69.

van der Geest, Rob J. et al., "Comparison Between Manual and Semiautomated Analysis of Left Ventricular Volume Parameters from Short–Axis MR Images", Journal of Computer Assisted Tomography, vol. 21, No. 5, 1997, pp. 756–765.

Weiss, Robert M. et al., "Evaluation of Cardiovascular Structure and Function with Electron–Beam ComputedTomography", Cardiac Imaging, 2: 820–828.

Xiaolong, Dai et al., "Left–Ventricle Boundary Detection from Nuclear Medicine Images", www4.ncsu.edu/eos/users/w/wes/homepage/daiHTML/cmrg$_{13}$JDI.fm3.html, Mar. 20, 2003, pp. 1–15.

* cited by examiner

Short axis reformat view

Regional Quantification

End Diastole — 640

End Systole — 642

METHOD AND APPARATUS FOR ACQUIRING AND ANALYZING CARDIAC DATA FROM A PATIENT

BACKGROUND OF THE INVENTION

This invention relates generally to an imaging system, and more particularly to a method and apparatus for use of the imaging system to acquire and analyze cardiac data of a patient.

Medical diagnostic and imaging systems are present in modern health care facilities. Such systems provide invaluable tools for identifying, diagnosing and treating physical conditions and greatly reduce the need for surgical diagnostic intervention. In many instances, final diagnosis and treatment proceed only after an attending physician or radiologist has complemented conventional examinations with detailed images of relevant areas and tissues via one or more imaging modalities.

Heart disease is a major cause of mortality in the United States and coronary artery disease (CAD), also known as ischemic heart disease, accounts for the majority of the heart ailments. Stable CAD is a result of stenosis of the coronary arteries that develops over time, which may result in chest pain when the demand for blood by the heart muscle (myocardium) increases and the coronary arteries are not able to meet the demand. It is estimated that in the United States alone there are as many as 16.5 million patients with stable CAD. In contrast to stable CAD, acute cardiac syndromes (ACS) develop suddenly and the symptoms include chest pain, shortness of breath, perspiration, and lightheadedness, all typically occurring while the person is at rest. The cause of ACS is typically a sudden formation of a clot (thrombus) in the coronary artery that produces either a partial block or a complete occlusion, with the result being ischemia, infarction, or necrosis (death of myocardial tissue). ACS is a dynamic process, and if untreated may have severe consequences, such as permanent damage to the myocardium, significant loss of myocardial function, or lethal arrhythmias. It is estimated that in the United States alone there are 2.3 million patients treated for ACS each year.

Presently available non-invasive analysis and diagnostic methods include echocardiography (Ultrasound), radionuclide imaging, magnetic resonance (MR) imaging, and computed tomography (CT) imaging, and with respect to heart disease, are typically limited to static analysis, analysis of a single heart condition, analysis with geometric approximations, or analysis based on operator input.

SUMMARY OF THE INVENTION

In one embodiment, a method for acquiring and analyzing cardiac data of a patient includes acquiring a first volume of cardiac data from a medical scanner, processing the first volume of cardiac data for image reconstruction and visualization, acquiring a subsequent plurality of volumes of cardiac data from the medical scanner, processing the subsequent plurality of volumes of cardiac data for image reconstruction and visualization, and reconstructing and visualizing first and second image sets from the acquired first and the subsequent plurality of volumes of cardiac data, respectively.

In another embodiment, an apparatus for the acquisition and analysis of cardiac image data is provided. The apparatus includes a medical scanner for generating first and second volumes of cardiac image data in a single exam, a data acquisition system for acquiring either the first or second volumes of cardiac image data, an image reconstructor for reconstructing a viewable image from either the first or second volumes of cardiac image data, a database for storing information from the data acquisition system and the image reconstructor, and an operator interface for managing either the medical scanner, the data acquisition system, the image reconstructor, or the database. A computer includes a post-processing algorithm for analyzing the reconstructed volume of cardiac image data and displaying the viewable image, the computer being responsive to the operator interface. The post-processing algorithm includes instructions for automatically delineating a region of the viewable image representative of either the myocardial muscle or the left ventricle, automatically volume rendering an image of either the myocardial muscle or the left ventricle, and automatically determining an image of a phase of the cardiac cycle representative of either end diastole or end systole.

BRIEF DESCRIPTION OF THE DRAWINGS

Referring now to the figures, which are exemplary embodiments, and wherein like elements are numbered alike.

DETAILED DESCRIPTION OF THE INVENTION

Detailed descriptions of embodiments of the present invention are presented herein by way of exemplification and not limitation with reference to the several Figures. The following description is provided with an example of cardiac imaging by computed tomography (CT). However, embodiments of this invention are applicable to all relevant cardiac imaging modalities including, but not limited to CT, magnetic resonance imaging, radionuclide imaging, echocardiography (Ultrasound), positron emission tomography (PET).

Figure 1:
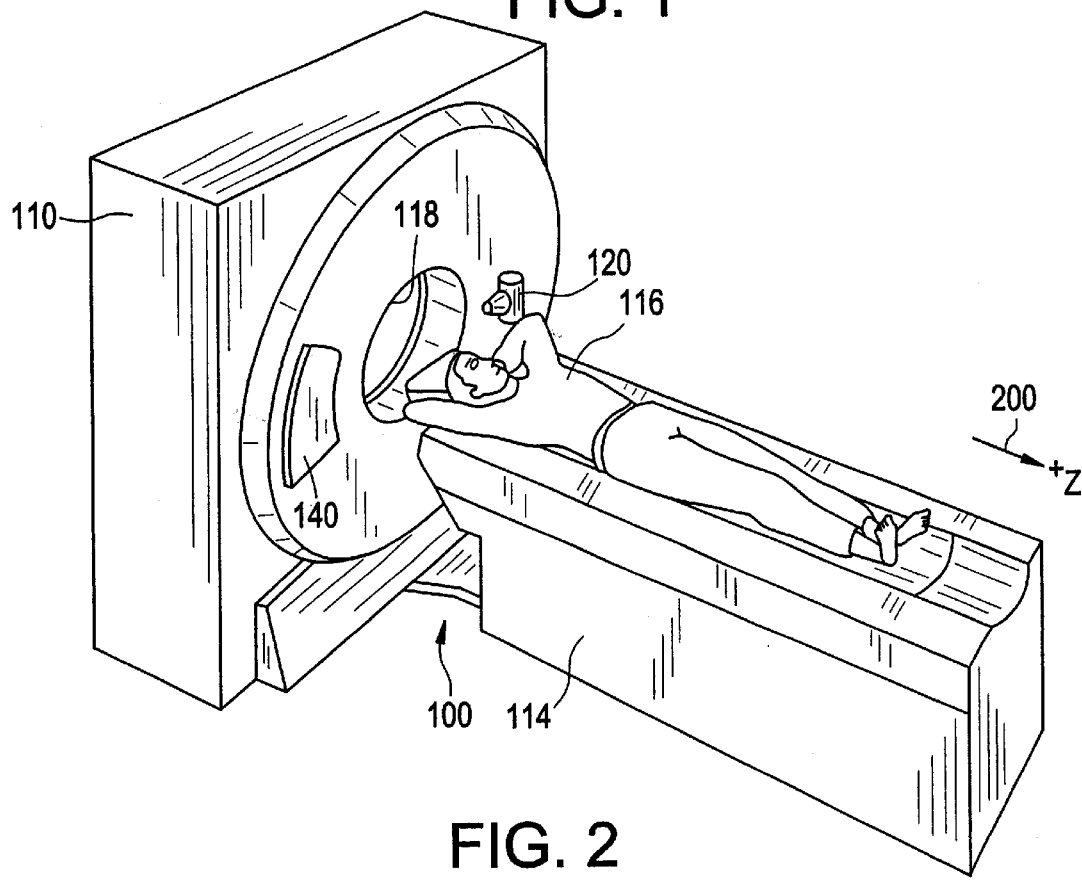
FIG. 1 depicts a generalized pictorial view of a CT imaging system for acquiring and analyzing cardiac data from a patient.
Figure 2:
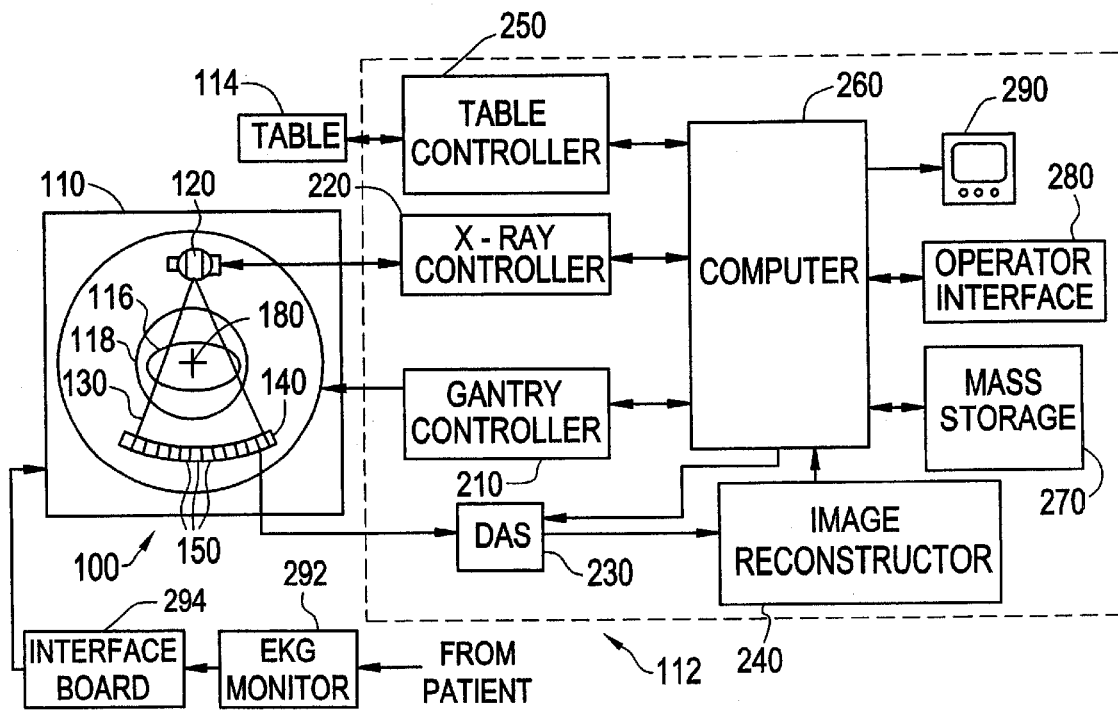
FIG. 2 depicts a generalized block schematic diagram of the imaging system of FIG. 1.

Referring to FIGS. 1 and 2, a computed tomograph (CT) imaging system 100 is shown having a gantry 110, which is representative of a CT scanner (scanner), a control system 112, and a motorized table 114 for positioning an object 116, such as a patient, in gantry opening 118 in gantry 110. Gantry 110 includes an x-ray source 120 that projects a fan beam of x-rays 130 toward a detector array 140 on the opposite side of gantry 110. Detector array 140 is formed by detector elements 150, which may include a single row or multiple rows of elements 150. Detector elements 150 are radiation detectors that each produce a signal having a magnitude that represents and is dependent on the intensity of the attenuated x-ray beam 130 after it has passed through patient 116 being imaged. During a helical scan that acquires x-ray projection data, the gantry 110 along with the x-ray source 120 and detector array 140 rotate within the imaging plane and around the patient 116 about a center of rotation 180, while the patient 116 is moved through the gantry in a z-direction 200 perpendicular to the imaging plane.

Gantry 110 and x-ray source 120 are controlled by control system 112, which includes a gantry controller 210, an x-ray controller 220, a data acquisition system (DAS) 230, an image reconstructor 240, a table controller 250, a computer 260, a mass storage (database) system 270, an operator interface 280, and a display device 290. Gantry controller 210 controls the rotational speed and position of gantry 110, x-ray controller 220 provides power and timing signals to x-ray source 120, data acquisition system 220 acquires analog data from detector elements 150 and converts the data to digital form for subsequent processing, image reconstructor 240 receives the digitized x-ray data from DAS 230 and performs an image reconstruction process for subsequent cardiac analysis, as discussed below, and table controller 250 controls motorized table 114 to position patient 116 in gantry opening 118.

Computer 260 is in operable communication with gantry controller 210, x-ray controller 220, and table controller 250 whereby control signals are sent from the computer to controllers 210, 220, 250 and information is received from the controllers by computer 260. Computer 260 also provides commands and operational parameters to DAS 230 and receives reconstructed image data from image reconstructor 240. In an alternative embodiment, DAS 230 and image reconstructor 240 may be integrated with computer 260. The reconstructed image data is stored by computer 260 in a mass storage device 270 for subsequent retrieval. An operator interfaces with computer 260 through operator interface 280, which may include, for example, a keyboard and a graphical pointing device, and receives output, such as, for example, a reconstructed image, control settings and other information, on a display device 290.

Figure 3:
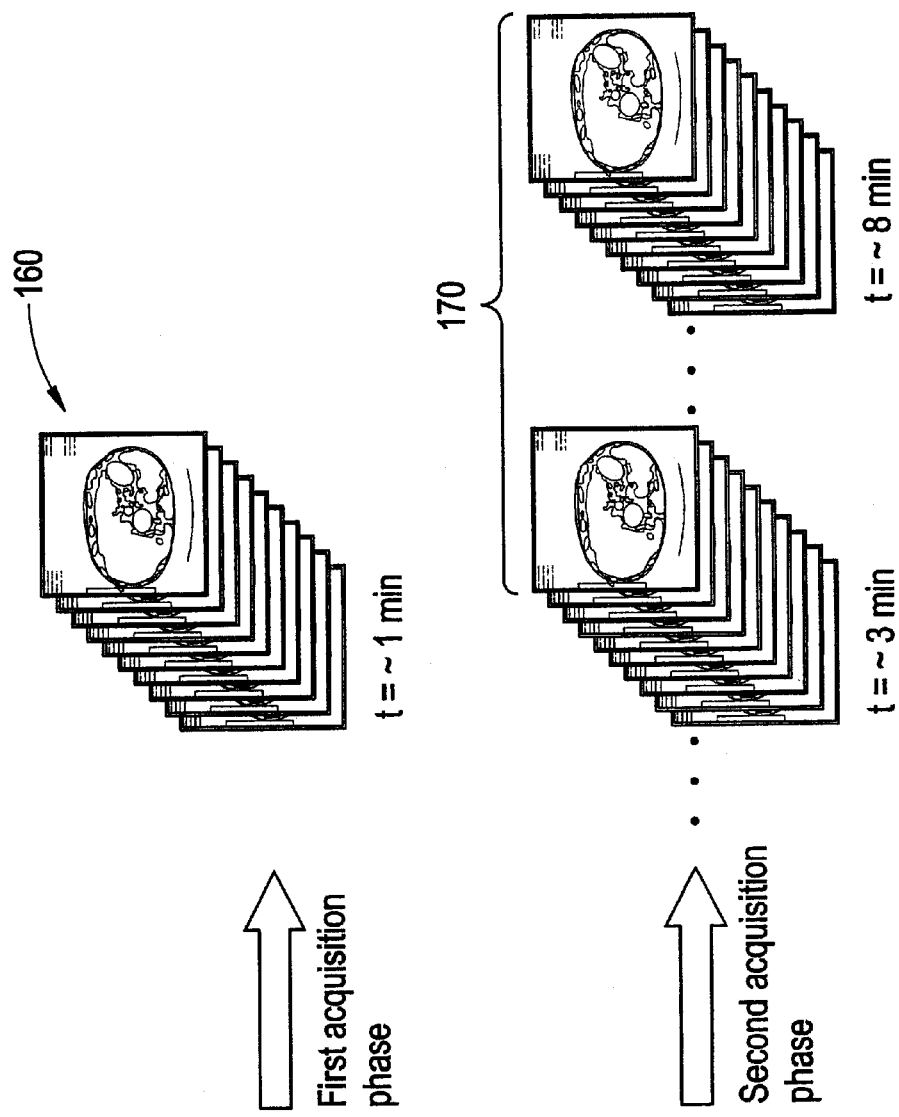
FIG. 3 depicts a generalized work flow for acquiring cardiac data from the system of FIG. 1.

Operable communication between the various system elements of FIG. 1 is depicted by arrowhead lines, which illustrate a means for either signal communication or mechanical operation, depending on the system element involved. Operable communication amongst and between the various system elements may be obtained through a hardwired or a wireless arrangement. Computer 260 may be a standalone computer or a network computer and may include instructions in a variety of computer languages for use on a variety of computer platforms, such as, for example, DOS™-based systems, Apple™-based systems, Windows™-based systems, HTML-based systems, or the like. FIG. 3 depicts a first volume of cardiac images 160 (a first image set from first acquisition phase) and a series of subsequent volumes of cardiac images 170 (a second image set from second acquisition phase) generated by CT imaging system 100 and control system 112. The time of acquisition of images 160 and 170 are shown in FIG. 3 to be 1-minute and 3–8 minutes, respectively, which are for exemplary purposes only.

CT imaging system 100 includes an electrocardiogram (EKG) monitor 292 that outputs R-peak events, which generally delineate the beginning of a heart cycle. The EKG monitor 292 is coupled to scanner 110 through an interface board 294 and enables synchronization between the scanner data and the EKG monitor data. Alternatively, the interface board 294 may be used to couple the EKG monitor 292 to scanner 110. An example of an interface board 294 is a Gantry interface board. The exemplary scanner 110 is a cardiac computed tomography (CT) system with support for cardiac imaging, however, the illustrated scanner 110 is for exemplary purposes only; other imaging systems known in the art may also be used. Examples of other imaging systems include, but are not limited to, X-ray systems (including both conventional and digital or digitized imaging systems), magnetic resonance (MR) systems, positron emission tomography (PET) systems, ultrasound systems, nuclear medicine systems, and 3D fluoroscopy systems. CT imaging system 100 also includes EKG gated acquisition or image reconstruction capabilities to image the heart free of motion artifact, typically in its diastolic phase for optimum image quality. CT imaging system 100 further includes circuitry for acquiring image data at DAS 230 where the data is transformed into a useable form and processed at image reconstructor 240 to create a reconstructed image of features of interest within the patient. The image data acquisition and processing circuitry is often referred to as a "scanner", regardless of the type of imaging system, because some sort of physical or electronic scanning often occurs in the imaging process. The particular components of the system and related circuitry differ greatly between imaging systems due to the different physics and data processing requirements of the different system. However, it will be appreciated that the present invention can be applied regardless of the selection of a particular imaging system.

Data are output from scanner 110 into control system 112 that includes software to perform data acquisition in data acquisition system 230, and image generation in image reconstructor 240. Data control is provided by operator interface 280. Data that is output from the scanner 110 is stored in mass storage 270. Data acquisition is performed according to one or more acquisition protocols that are optimized for imaging the heart, and specifically for imaging the left ventricle and myocardial muscle. Image generation in image reconstructor 240 is performed using one or more optimized 3D protocols for automated post-processing of the CT image dataset.

Computer 260 includes known visualization algorithms for use with medical CT imaging data, such as, for example, multiplanar volume reformat (MPVR), Maximum Intensity Projection (MIP), 3D surface rendering or volume rendering (VR), and immersible viewing (i.e., viewing from the inside), which can be used for detecting vessel stenosis. A variety of 3D software packages for volume analysis and cardiac image quality analysis are also available.

Embodiments of the present invention employ the programs on computer 260 for the acquisition and post-processing of cardiac data relating to coronary artery disease, acute cardiac syndromes, coronary artery imaging, cardiac function analysis, myocardial perfusion analysis, myocardial perfusion defect analysis, automated left ventricle delineation, automated volume rendering, automated cardiac phase selection, end diastole volume analysis, end systole volume analysis, stroke volume analysis, ejection fraction analysis, and cardiac output analysis, all from a single cardiac CT scan, as discussed in detail below.

Figure 4:
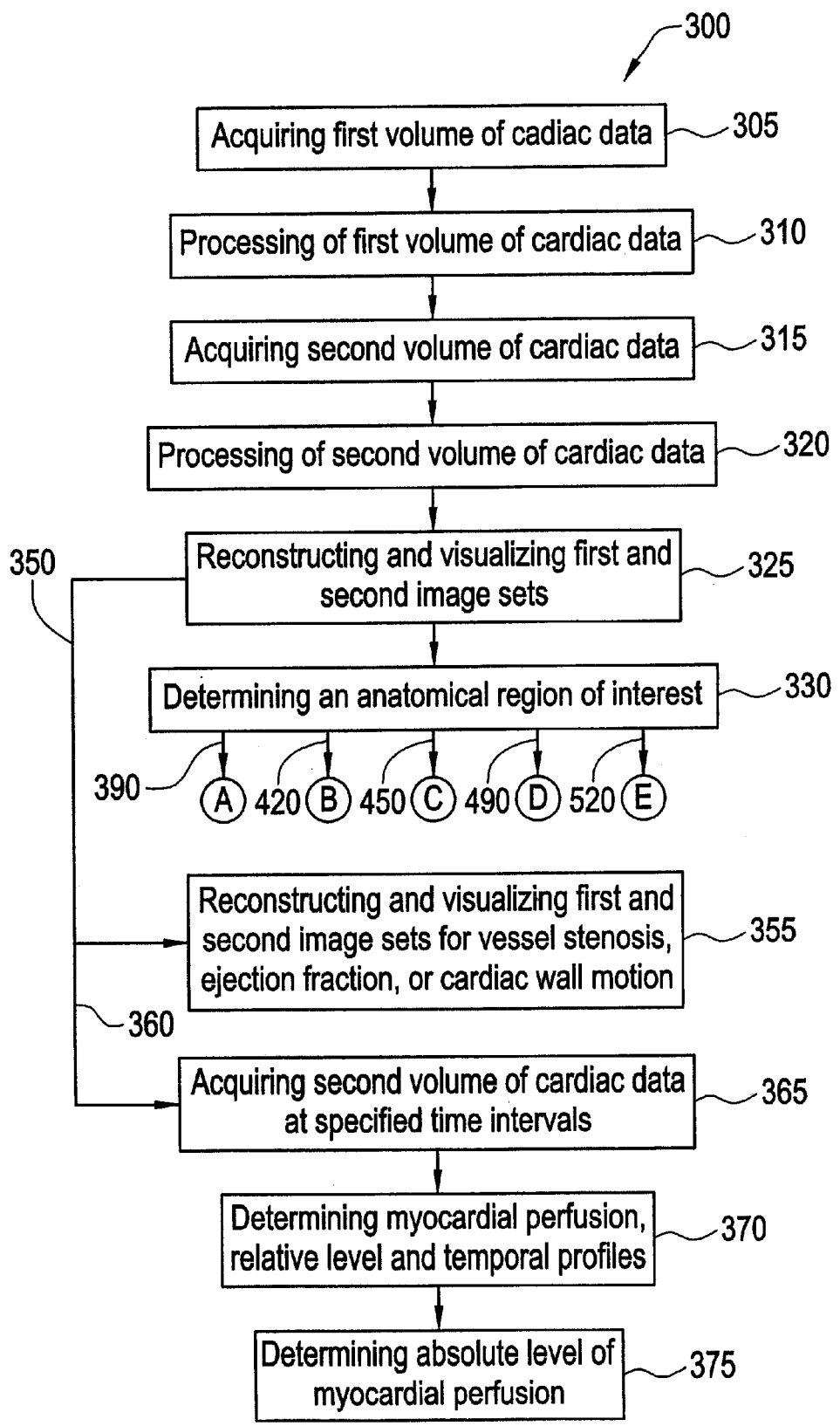
FIG. 4 depicts a flowchart of a process for acquiring and analyzing cardiac data from the system of FIG. 1.

In an embodiment of the present invention, and referring now to FIG. 4, a process 300 for acquiring and analyzing cardiac data of a patient begins at step 305 where CT imaging system 100 and DAS 230 perform a first scan, first acquisition phase, to acquire a first volume of cardiac data, which is typically acquired in the absence of absorbed contrast enhancing media. Contrast enhancing media may be injected into the patient prior to or subsequent to the initial scanning and is used to enhance the contrast between reconstructed images of bodily tissues that absorb the contrast media at different rates. The absence of contrast media in the first volume of cardiac data may be the result of media injection subsequent to the initial scanning, or the result of delayed absorption of the media with injection occurring prior to the initial scanning. The first volume of cardiac data is typically used as a baseline, generally involves a single pass, or scan, of the heart over the course of a single heart cycle, and is used to generate first volume of cardiac images 160. By optimizing the contrast injection rate to patient 116, prolonged image enhancement can be achieved, thereby enabling subsequent anatomical scans to be conducted for providing myocardial perfusion information along with coronary artery imaging data and cardiac function data, as will be discussed below.

At step 310, processing of the first volume of cardiac data for image reconstruction and visualization is performed by image reconstructor 240 and computer 260 using known image reconstruction algorithms. The processed data from step 310 is stored at mass storage system 270.

At step 315, a subsequent volume of cardiac data from CT imaging system 100 is acquired, which is referred to as a second acquisition phase and is typically a series of dynamic scanning passes. It will be appreciated that reference to a subsequent volume of cardiac data also encompasses a second volume, at least a second volume, or a series of subsequent volumes of cardiac data, and is intended to reflect the generation of at least one additional volume, and usually more than one, of cardiac data subsequent to the generation of the first volume. Subsequent volumes of cardiac data are used to generate subsequent volumes of cardiac images 170. The subsequent volume of cardiac data is typically acquired in the presence of absorbed contrast enhancing media, and with the acquisition of a series of subsequent volumes of cardiac data, the rate of absorption of the contrast media at various anatomical regions can be analyzed and used for various diagnoses, as will be discussed below. The subsequent volumes of cardiac data may be representative of the same anatomical region of interest as depicted in the first volume of cardiac data from the first scan, or a subset thereof. The subsequent volume of cardiac data may be acquired at a scan slice thickness greater than the scan slice thickness used for acquiring the first volume of cardiac data, thereby covering the desired region of interest in subsequent passes within a fixed amount of time.

At step 320, and similar to step 310, processing of the subsequent volume of cardiac data for image reconstruction and visualization is performed by image reconstructor 240 and computer 260. The processed data from step 320 is also stored at mass storage system 270.

At step 325, first and second image sets 160, 170, from the first and subsequent volumes of cardiac data, respectively, are reconstructed and visualized using known software. Mass storage system 270 is used to store image sets 160, 170.

At step 330, the user determines, from the first volume of cardiac data, which anatomical region of interest, such as, for example, the coronary artery, the left ventricle, and the myocardial muscle, is to be used for subsequent analysis and post-processing.

In another embodiment, and referring now to alternative path 350 of FIG. 4, first image set 160 can be reconstructed and visualized 355 for detecting vessel stenosis in the coronary arteries using currently available methods, such as, for example, using the best phase of the heart cycle to reduce motion artifacts produced by the beating of the heart, and techniques to produce reformatted views in various planes and 3D renderings. Additionally, the first image set 160 can be reconstructed and visualized 355 for the analysis of cardiac function, such as, for example, ejection fraction or cardiac wall motion, over multiple phases of the heart cycle.

In a further embodiment, and referring now to alternative path 360 in FIG. 4, the subsequent volumes of cardiac data from CT imaging system 100, which may also consist of a series of volumes of cardiac data, are acquired 365 at specified time intervals from the time of contrast injection, thereby establishing a time base for the resulting subsequent volumes of cardiac images 170 that are reconstructed and visualized. FIG. 3 shows a first and a last subsequent volume of cardiac data with acquisition times of 3-minutes and 8-minutes, respectively. Other volumes of images may be acquired at 4, 5, 6, and 7, minute intervals, thereby establishing a 1-minute time increment for generating a temporal profile of medical data. As discussed above, the times indicated herein, including FIG. 3, are for exemplary purposes only, and may be adjusted according to the specific medical condition being studied.

At step 370, images 160, 170 are analyzed to determine the degree of myocardial perfusion. This is accomplished by first employing an enhancement detection algorithm to differentiate enhanced regions of the myocardium from other regions of the heart, an edge detection algorithm to identify contours of the inner and outer walls of the myocardium, and a segmentation algorithm to separate the myocardial musculature. Once the myocardial musculature is segmented, enhancement of the cardiac tissue due to the presence of contrast is measured in different regions of the myocardium at different time intervals, thereby enabling the diagnosis of poorly perfused areas due to myocardial ischemia or infarction relative to the normally perfused areas, as well as poor temporal perfusion. For example, in the initial scan, first acquisition phase, approximately 1-minute (min) after contrast injection, a region of ischemia or infarction would display as a lower density area relative to a normally perfused tissue.

Figure 5:
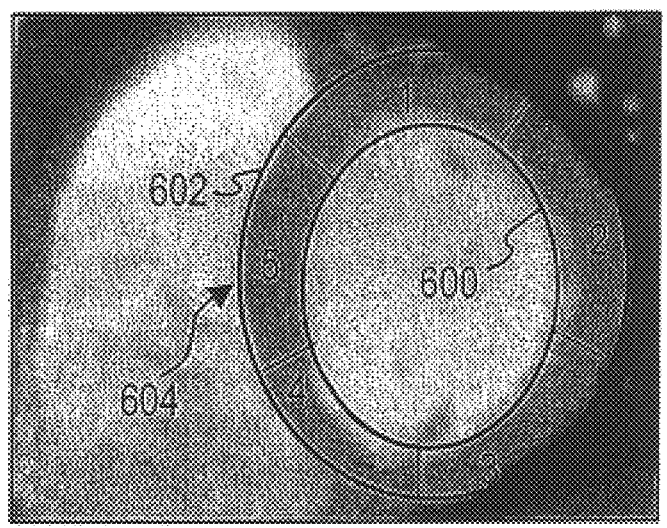
FIG. 5 depicts a short axis reformat view of the myocardial muscle in accordance with an embodiment of the invention.
Figure 6:
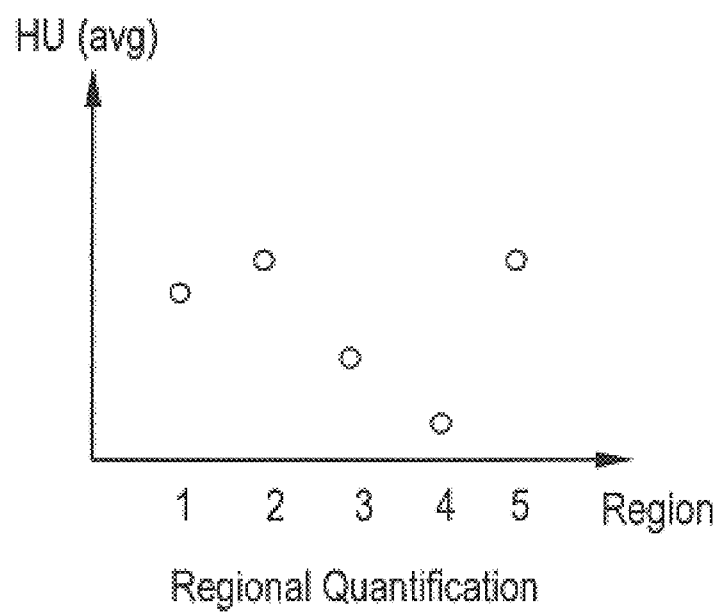
FIG. 6 depicts a plot of contrast enhancement (average) with respect to the view depicted in FIG. 5.

At step 375, the absolute level of myocardial perfusion is determined by comparing the model data against control data established for an age and gender-matched control population prior to the test. At a subsequent scan, 3-minutes post contrast injection for example, partial enhancement of the ischemic or infarcted (poorly perfused) area may be shown as the contrast gradually enters the tissue, while the normally perfused tissue would start to reduce in enhancement due to wash-out of the contrast. At a further subsequent scan, 8-minutes post contrast injection for example, the ischemic or infarcted area would present as a high density area due to contrast retention, relative to a normally perfused myocardium where the contrast would have cleared from the normal tissue. FIG. 5 shows a planar short axis reformat view through the heart where the inner 600 and outer 602 walls of the myocardium are delineated through edge detection, and the myocardial muscle segmented through segmentation, thereby enabling visualization of high and low contrast density areas shown as regions 1–5, numeral 604, for perfusion analysis. FIG. 6 depicts a contrast enhancement intensity plot (average values), in Hounsfield Units (HU) for regions 1–5 of FIG. 5.

Figure 7:
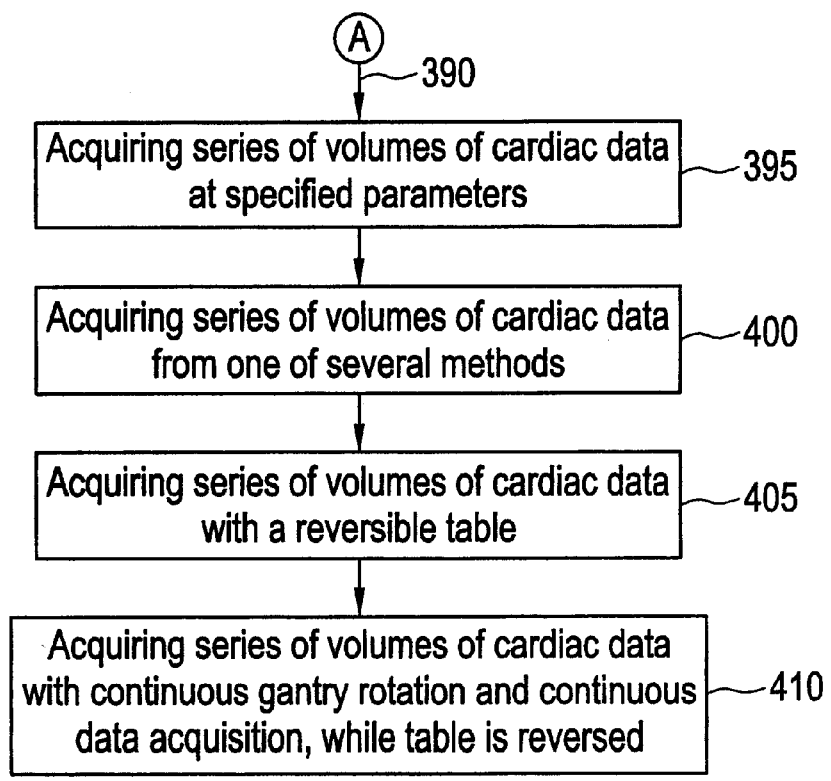
FIGS. 7–9 depict flowcharts of alternative embodiments of the process of FIG. 4.

In another embodiment, and referring now to alternative path 390 in FIGS. 4 and 7, the subsequent series of volumes of cardiac data, from the second acquisition phase, is acquired 395 by scanning the anatomical region of interest at least once per specified interval of time, one second for example, at a specified scan slice thickness, user defined, and for a specified number of scan slices, designated as N, and repeating the procedure for a specified total duration of time, 25–30 seconds for example.

At step 400, alternative methods by which the subsequent series of volumes of cardiac data may be acquired are provided, which include, for example, a cine scan method (scanning continuously without table movement), an axial scan method (scanning one rotation, moving to the next location, and repeating the process), and a helical scan method (spiral scan). The method of choice may be predetermined by the type of system employed, or may be selected by the user at the beginning of the study.

At step 405, and under conditions where an axial or helical scan method is employed, the acquisition of the successive series of volumes of cardiac data is performed with the capability that patient table 114 can be reversed after each series of scans, thereby avoiding delay between successive series of scans.

At step 410, and during the reverse motion of patient table 114, the acquisition of the successive series of volumes of cardiac data is performed while gantry 110 is continuously rotated and the scan data is continuously acquired.

Figure 8:
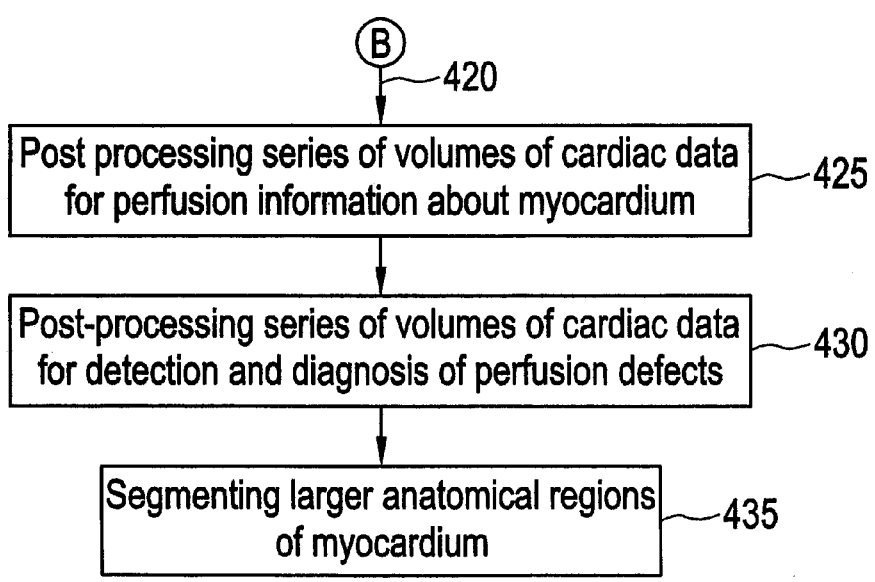

In yet a further embodiment, and referring now to alternative path 420 in FIGS. 4 and 8, post-processing 425 is performed on the series of volumes of cardiac data for visualization and analysis of information relating to perfusion within the myocardium.

At step 430, post-processing on the series of volumes of cardiac data continues with the creation of a series of short-axis reformatted images and volume-rendered 3D images of the heart, the segmentation of an anatomical region of the heart, the partitioning of the anatomical region into segments of interest for providing information relating to the detection and diagnosis of perfusion defects in the areas of the myocardium that are perfused by different coronary arteries and their branches or perfused by the role of collaterals, and the visualization of the degree of perfusion in the anatomical region by comparing regions of high and low contrast-enhancement.

At step 435, segmentation of the anatomical region of the heart may include the segmentation of larger regions of the myocardium, such as, the septum (superior and posterior), the right ventricle (base and apex), and the left ventricular (anterior, lateral, inferior, posterior, or combinations thereof).

Figure 9:
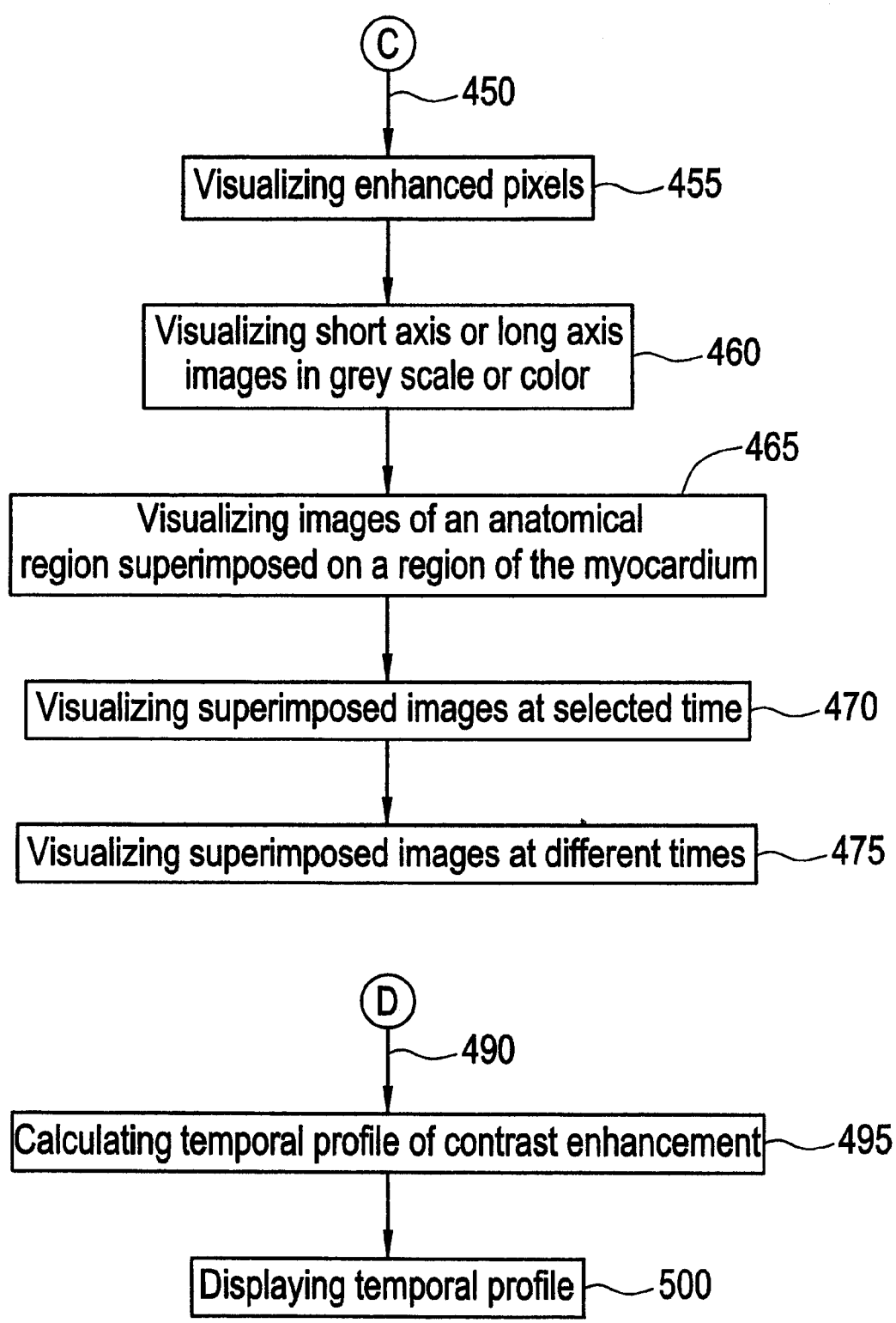

In another embodiment, and referring now to alternative path 450 in FIGS. 4 and 9, visualization of the degree of perfusion is performed by visualizing 455 enhanced pixels in response to the contrast enhancing media. The enhanced pixels are measured in Hounsfield units (HU).

Figure 10:
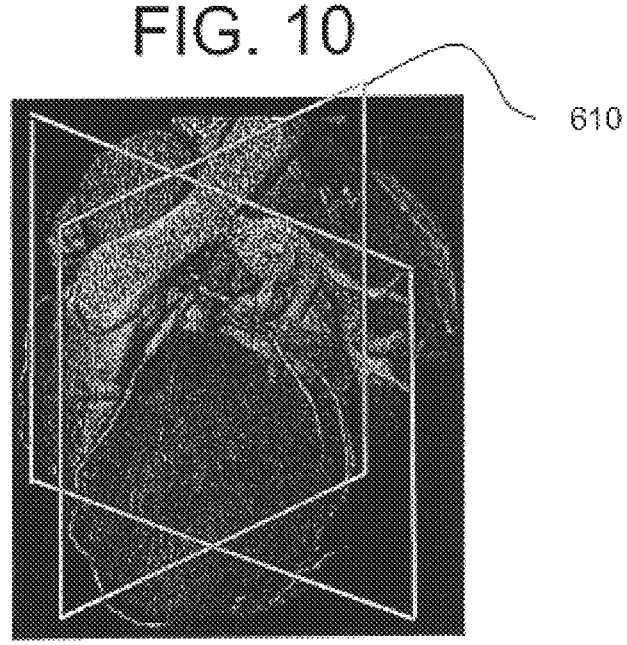
FIG. 10 depicts an isometric view of the heart with long axis section planes displayed.

At step 460, the enhanced pixels depicting short axis images or long axis images of the heart may be visualized in a grey scale or a color scheme. FIG. 10 depicts an isometric view of the heart with long axis section planes 610 displayed. These and other plane cuts may be used to investigate a variety of regions of interest in the heart, such as the septum, right ventricle, left ventricle, and myocardium for example. Short axis section planes (not shown) are cut at a 90-degree angle to the long axis section planes.

At step 465, images of enhanced pixels of an anatomical region of interest may be visualized by superimposing them on a region of interest of the myocardium.

At step 470, the superimposed images are visualized at a selected point in time, such as during end systole for example, which may be selected by the user during post-processing or by the user in response to a system prompt from computer 260.

At step 475, the superimposed images are visualized at different points in time, thereby showing the dynamic changes of perfusion over time and over the duration of time involved in acquiring the series of volumes of cardiac data. Such presentations provide a clear indication of the perfusion levels of the various regions of interest and thus enable the clinician to make differential diagnosis of the perfusion defects between the regions of interest. Intensity maps computed from the enhanced superimposed images enable cine presentation of dynamic changes of the perfusion during the entire duration of the second acquisition phase.

Using normal ranges of perfusion rates from healthy control groups, information from patients suspected of cardiac abnormalities can be evaluated for possible intervention.

In a further embodiment, and referring now to alternative path 490 in FIGS. 4 and 8, a temporal profile of contrast enhancement is calculated 495 for the data from the second acquisition phase. From user-selected parameters, the temporal profile can be used for measuring the time to reach a specified level of enhancement at a contrast enhanced anatomical region, such as the myocardium for example.

Figure 11:
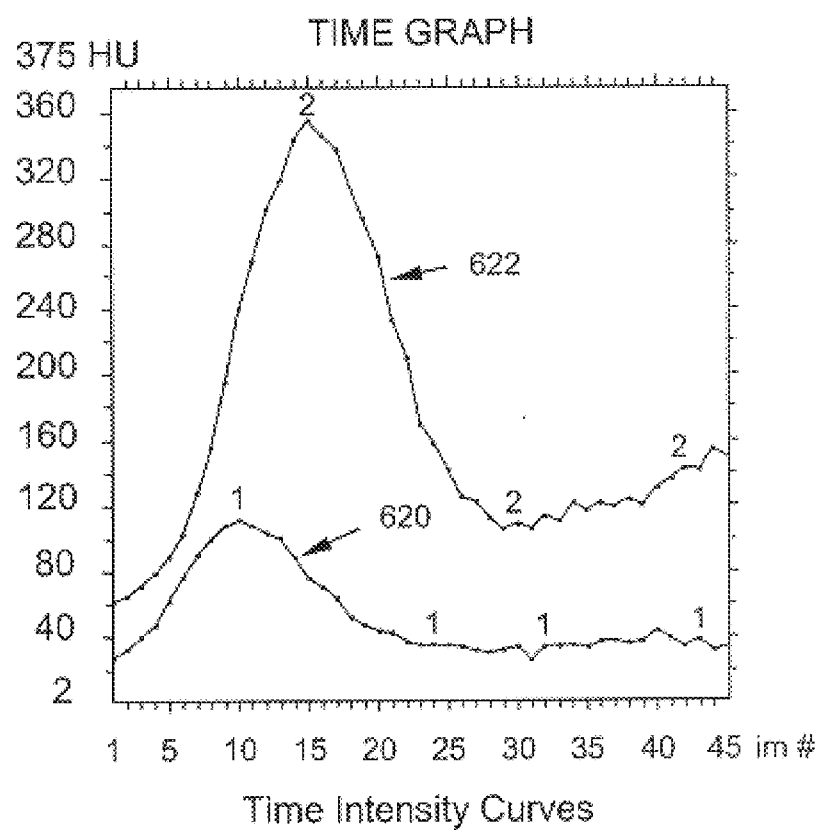
FIG. 11 depicts temporal profiles of contrast enhancement for different regions of the myocardial muscle in accordance with an embodiment of the invention.
Figure 12:
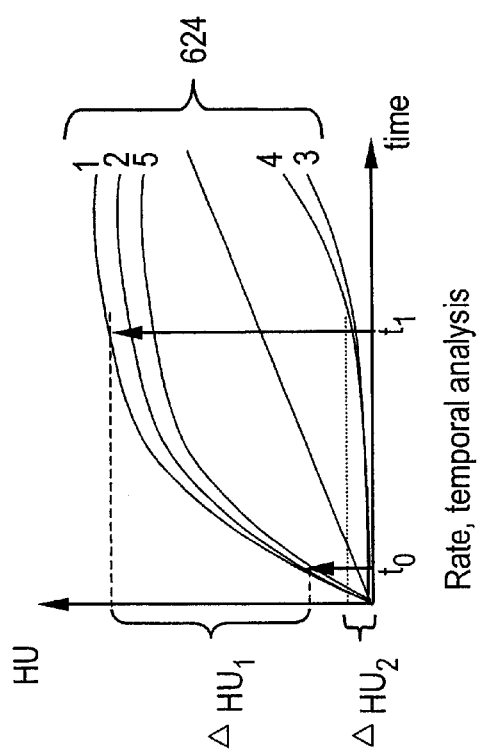
FIG. 12 depicts a temporal rate analysis for the contrast intensity in regions of the myocardial muscle.

At step 500, the temporal profile is plotted and displayed, as depicted for Region-1 620 and Region-2 622 in FIG. 11, which shows contrast enhancement in Hounsfield Units (HU) plotted against time (min). The temporal profile of contrast enhancement is indicative of potential tissue perfusion abnormalities. Such profiles can provide a quantitative assessment of the arrival and washout of contrast in different regions of interest, thereby providing a valuable tool for the diagnosis of perfusion defects and tissue viability. FIG. 12 depicts a temporal rate analysis for the contrast intensity, in HU, for Regions 1–5 of FIG. 5, numeral 624 in FIG. 12 and numeral 604 in FIG. 5.

Figure 13:
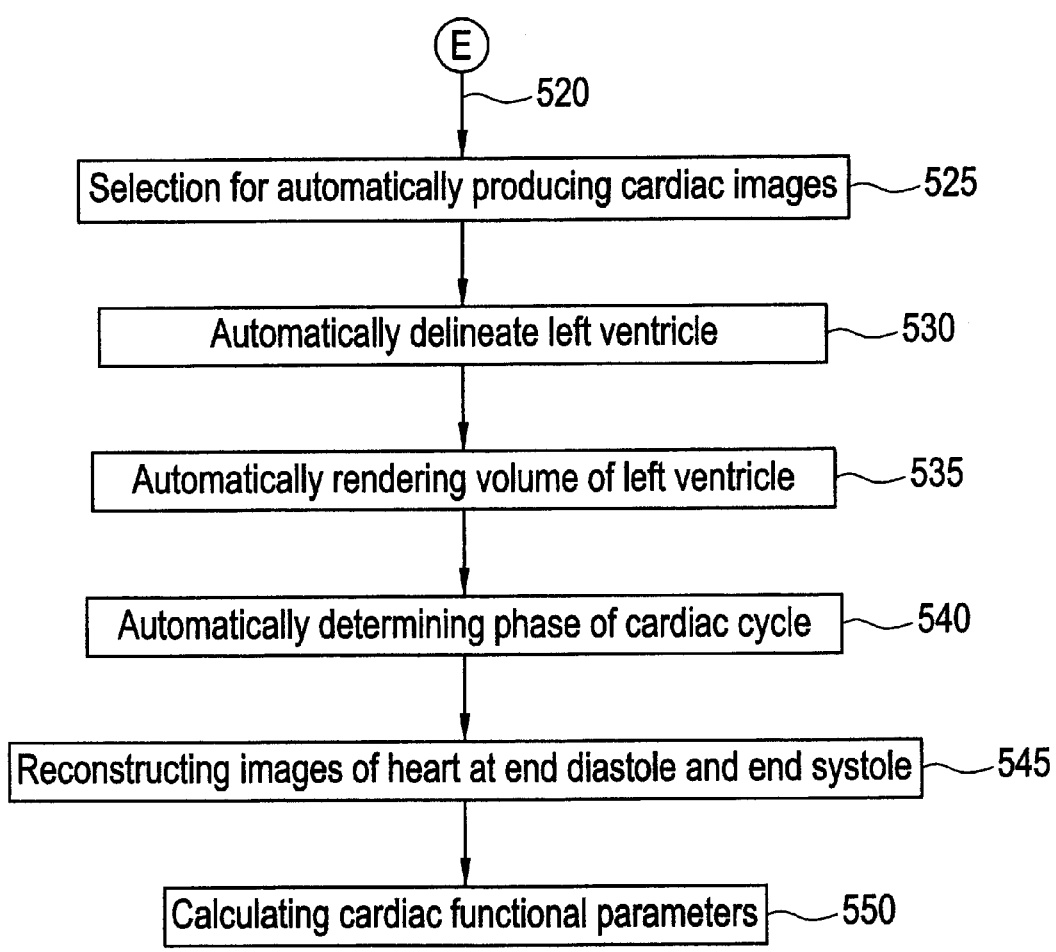
FIG. 13 depicts a flowchart of an alternative embodiment of the process of FIG. 4.

In another embodiment, and referring now to alternative path 520 in FIGS. 4 and 13, the post-processing of the data from the first and second acquisition phases includes a selection for automatically producing 525 images of the heart at end diastole and end systole for visualization and functional analysis.

At step 530, the post-processing algorithm automatically delineates 530 a region representative of the myocardial muscle within one of the ventricles, and specifically within the left ventricle. The automated delineation is accomplished by the post-processing algorithm first identifying a first contrast enhanced region having a first level of contrast enhancement, such as the myocardial muscle, from a second contrast enhanced region having a second level of contrast enhancement, such as the inner volume of the left ventricle. Next, the algorithm assigns the first contrast enhanced region to the region representative of the myocardial muscle for determining a myocardial muscle volume, and the second contrast enhanced region to the region representative of the left ventricle absent the myocardial muscle for determining a left ventricle volume. The post-processing software uses a combination of tracking algorithms such as thresholding (contrast intensity in excess of a specified threshold), edge or contour detection (transition point between regions of high and low contrast enhancement), and region growing (change in quantity of enhanced pixels).

At step 535, post-processing continues by the algorithm automatically rendering the volume of the left ventricle and myocardial muscle, which can be performed at any specified phase of the cardiac cycle, but is typically performed at end diastole and end systole. The automated volume rendering is accomplished by either the user first selecting a cardiac region of interest for volume rendering or the algorithm automatically identifying the region of interest. Once the region of interest is selected, the algorithm acquires the cardiac volume data, reconstructs an image of the cardiac region of interest at the selected cardiac phase in a 3D model, and then displays the reconstructed 3D model image.

Figure 14:
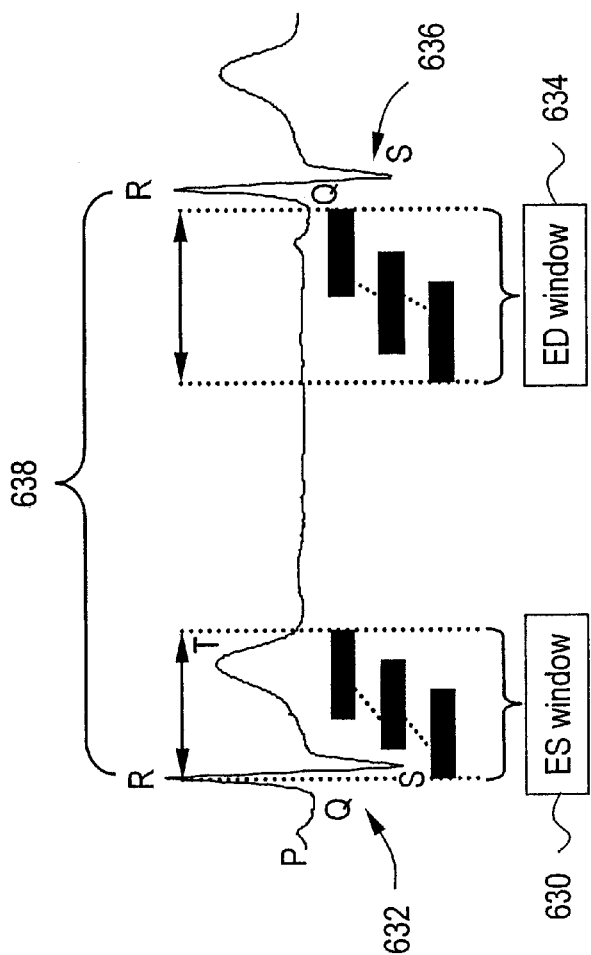
FIG. 14 depicts an EKG output showing end systole and end diastole.

At step 540, post-processing continues by automatically determining which image in the phase of the cardiac cycle represents end diastole and end systole. This automated determination is accomplished by the algorithm applying the output of EKG monitor 292 as a reference for identifying the time windows in the cardiac cycle representative of end systole and end diastole, determining from the data of the first and second acquisition phases which image of the phase of the cardiac cycle has the largest left ventricle volume (largest volume of contrast enhancement for the left ventricle volume), determining from the data of the first and second acquisition phases which image of the phase of the cardiac cycle has the smallest left ventricle volume (smallest volume of contrast enhancement for the left ventricle volume), designating the image of the phase of the cardiac cycle having the largest left ventricle volume as end diastole, and designating the image of the phase of the cardiac cycle having the smallest left ventricle volume as end systole. The end systole (ES) time window 630 is defined by the EKG reading following a first QRS 632, and the end diastole (ED) time window 634 is defined by the EKG reading prior to a second QRS 636, as shown in FIG. 14. In reference to FIG. 14, it will be appreciated that a phase location is a prescribed percentage of the R—R interval 638 representing a point in time of the heartbeat.

At step 545, the post-processing algorithm reconstructs, using known image reconstruction methods, images of the heart at the end diastole and end systole phases and displays the reconstructed images.

Figure 15:
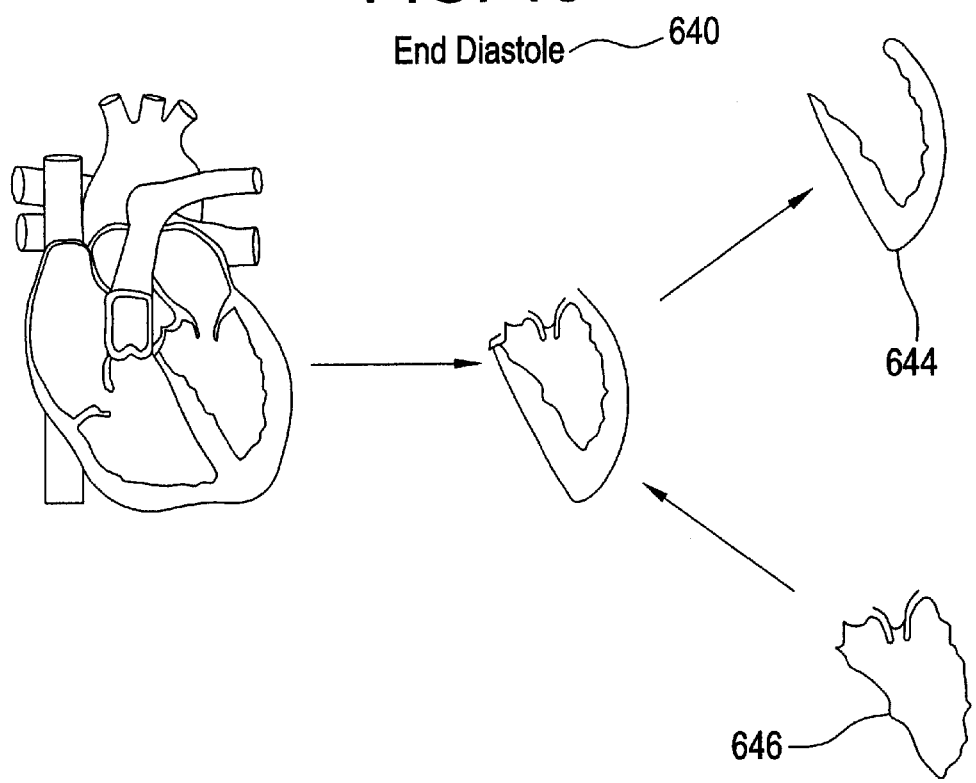
FIGS. 15 and 16 depict views of the heart at end diastole and end systole, respectively, with the myocardial muscle delineated in accordance with an embodiment of the invention.
Figure 16:
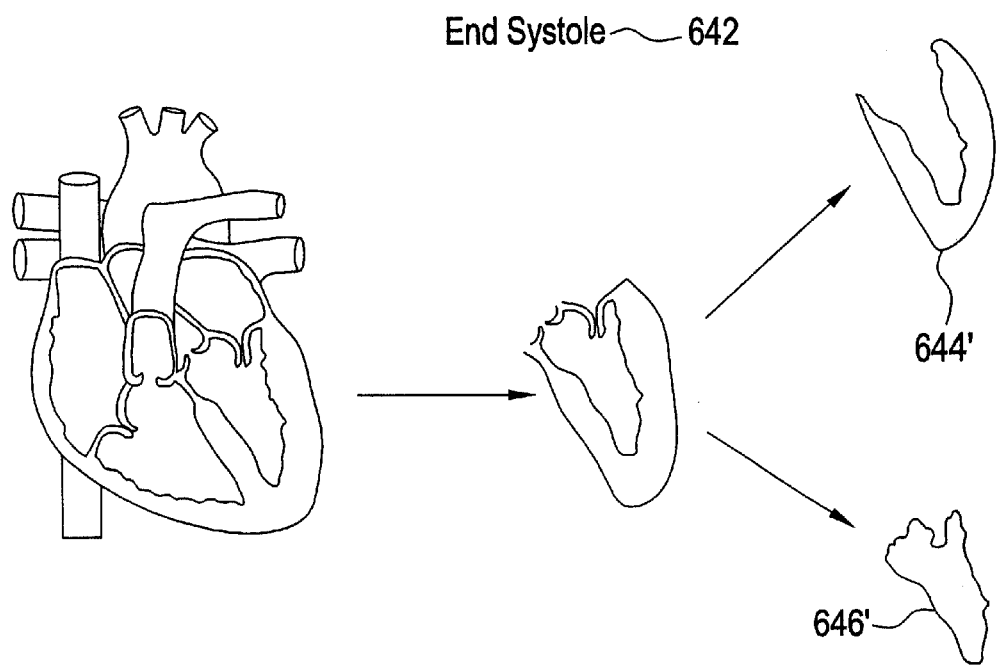

At step 550, the post-processing algorithm calculates cardiac functional parameters, such as, end diastole volume, end systole volume, stroke volume, ejection fraction, cardiac output, myocardial muscle wall thickness, left ventricle volume, and motion of the myocardial muscle wall. For this calculation, volume rendering techniques in 3D space are employed to provide a quantitative analysis of the contrast contained within the ventricle at both end systole and end diastole. FIGS. 15 and 16 depict views of the heart at end diastole 640 and end systole 642, respectively, where contour detection and region segmentation algorithms have been employed to identify and segment the myocardial muscle 644, 644', leaving the left ventricle (LV) volume 646, 646' as a region of interest for volume analysis. LV volume 646 in FIG. 15 is depicted having a larger volume than LV volume 646' in FIG. 16, which is consistent with the ED and ES phases.

Figure 17:
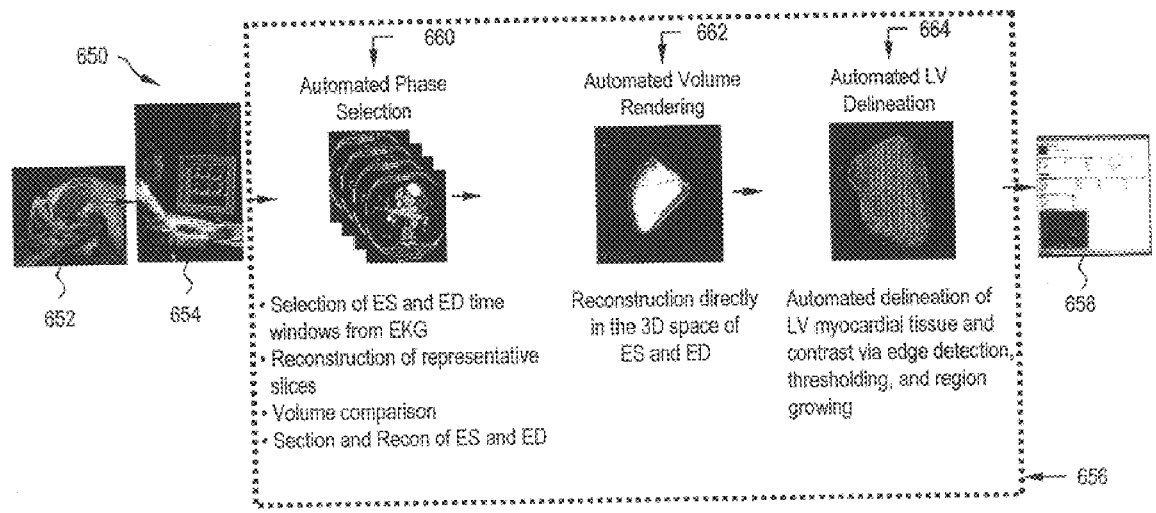
FIG. 17 depicts a generalized schematic flowchart of a cardiac analysis process in accordance with an embodiment of the invention.

FIG. 17 depicts a generalized schematic flowchart of the cardiac analysis process 650 including data acquisition 652, processing 654, automated post-processing analysis 656, and post-processing analysis and reporting 658. Included in the automated post-processing analysis 656 is: automated phase selection 660, automated volume rendering 662, and automated left ventricle (LV) delineation 664. The cardiac analysis process 650 provides for an accurate non-invasive way to measure cardiac function and ventricular wall thickness using computed tomographic images.

The selection of an alternative path 350, 360, 390, 420, 450, 490, 520 is preferably accomplished by the user selecting a response to a system prompt from computer 260 at a defined point in the process 300, however, the selection may also be accomplished by a user-initiated action.

The data acquisition and analysis, and image reconstruction and visualization, depicted in FIGS. 3, 5, 6, 10, 11, 12, 14, 15, 16, 17, may be accomplished using 0.5 second (sec) Gantry periods, 0.5 millimeter (mm) image thickness, 120 kilovolt (kV), 80 milliamp (mA), 0.1 sec recon interval, with ECG (Electrocardiograph) wave data synchronization.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An apparatus for the acquisition and analysis of cardiac image data, comprising:
    a medical scanner for generating first and second volumes of cardiac image data in a single exam;
    a data acquisition system for acquiring at least one of said first or second volumes of cardiac image data;
    an image reconstructor for reconstructing a viewable image from at least one of said first or second volumes of cardiac image data;
    a database for storing information from said data acquisition system and said image reconstructor;
    an operator interface for managing at least one of said medical scanner, said data acquisition system, said image reconstructor, or said database;
    a computer comprising at least one post-processing algorithm for analyzing the reconstructed volume of cardiac image data and displaying said at least one viewable image, said computer being responsive to said operator interface; and
    said post-processing algorithm comprising instructions for automatically delineating a region of said at least one viewable image representative of at least one of the myocardial muscle or the left ventricle, automatically volume rendering an image of at least one of the myocardial muscle or the left ventricle, and automatically determining an image of a phase of the cardiac cycle representative of at least one of end diastole or end systole.

2. A method for acquiring and analyzing cardiac data of a patient, comprising:
    acquiring a first volume of cardiac data from a medical scanner in the absence of absorbed contrast enhancing media;
    processing the first volume of cardiac data for image reconstruction and visualization;
    acquiring a series of volumes of cardiac data from the medical scanner in the presence of absorbed contrast enhancing media and at specified time intervals from the time of contrast injection;
    processing the series of volumes of cardiac data for image reconstruction and visualization;
    reconstructing and visualizing a first image set from the acquired first volume of cardiac data and a series of image sets at specified time intervals from the time of contrast injection from the acquired series of volumes of cardiac data; and
    determining myocardial perfusion by segmenting contours of the myocardium and comparing the tissue enhancement in the region between the segmented contours over a plurality of image sets.

3. The method of claim 2, further comprising:
    determining absolute levels of myocardial perfusion by comparing the tissue enhancement in the region between the segmented contours to expected normal perfusion levels established for a control population.

4. A method for acquiring and analyzing cardiac data of a patient, comprising:
    acquiring a first volume of cardiac data over the course of at least one heart cycle from a single pass of the heart by a medical scanner in the absence of absorbed contrast enhancing media;
    processing the first volume of cardiac data for image reconstruction and visualization;
    determining an anatomical region of interest from the acquired first volume of cardiac data;
    acquiring a series of volumes of cardiac data, representative of at least a subset of the anatomical region of interest, from the medical scanner, at a scan slice thickness greater than the scan slice thickness used for said acquiring a first volume of cardiac data, in the presence of absorbed contrast enhancing media;
    processing the series of volumes of cardiac data for image reconstruction and visualization; and
    reconstructing and visualizing a first and at least a second image set from the acquired first and series of volumes of cardiac data, respectively.

5. A method for acquiring and analyzing cardiac data of a patient, comprising:
    acquiring a first volume of cardiac data from a medical scanner;
    processing the first volume of cardiac data for image reconstruction and visualization;
    acquiring at least a second volume of cardiac data from the medical scanner;
    processing the at least a second volume of cardiac data for image reconstruction and visualization;
    reconstructing and visualizing a first and at least a second image set from the acquired first and at least a second volumes of cardiac data, respectively; and
    determining myocardial perfusion by segmenting contours of the myocardium and comparing the tissue enhancement in the region between the segmented contours over a plurality of image sets.

6. A method for acquiring and analyzing cardiac data of a patient, comprising:
    acquiring a first volume of cardiac data from a medical scanner;
    processing the first volume of cardiac data for image reconstruction and visualization;
    acquiring at least a second volume of cardiac data from the medical scanner at a scan slice thickness greater than the scan slice thickness used for said acquiring a first volume of cardiac data;
    processing the at least a second volume of cardiac data for image reconstruction and visualization; and
    reconstructing and visualizing a first and at least a second image set from the acquired first and at least a second volumes of cardiac data, respectively.

7. A method for acquiring and analyzing cardiac data of a patient, comprising:

acquiring a first volume of cardiac data from a medical scanner;

processing the first volume of cardiac data for image reconstruction and visualization;

acquiring at least a second volume of cardiac data from the medical scanner;

processing the at least a second volume of cardiac data for image reconstruction and visualization;

reconstructing and visualizing a first and at least a second image set from the acquired first and at least a second volumes of cardiac data, respectively; and post-processing the at least a second volume of cardiac data for visualization and analysis of information relating to perfusion.

8. A method for acquiring and analyzing cardiac data of a patient, comprising:

acquiring a first volume of cardiac data from a medical scanner;

processing the first volume of cardiac data for image reconstruction and visualization;

acquiring at least a second volume of cardiac data from the medical scanner;

processing the at least a second volume of cardiac data for image reconstruction and visualization;

reconstructing and visualizing a first and at least a second image set from the acquired first and at least a second volumes of cardiac data, respectively; and delineating a region representative of the myocardial muscle within at least one ventricle.

9. A method for acquiring and analyzing cardiac data of a patient, comprising:

acquiring a first volume of cardiac data over the course of at least one heart cycle from a single pass of the heart by a medical scanner in the absence of absorbed contrast enhancing media;

processing the first volume of cardiac data for image reconstruction and visualization;

acquiring at least a second volume of cardiac data from the medical scanner in the presence of absorbed contrast enhancing media;

processing the at least a second volume of cardiac data for image reconstruction and visualization;

reconstructing and visualizing a first and at least a second image set from the acquired first and at least a second volumes of cardiac data, respectively;

determining an anatomical region of interest from the acquired first volume of cardiac data;

post-processing at least one of the first volume or the at least a second volume of cardiac data to produce cardiac images for visualization and functional analysis; and delineating a region representative of the myocardial muscle within at least one ventricle.

10. The method of claim 9, wherein said delineating a region comprises:

identifying a first contrast enhanced region having a first level of contrast enhancement from a second contrast enhanced region having a second level of contrast enhancement;

separating the first and second contrast enhanced regions;

assigning the first contrast enhanced region to the region representative of the myocardial muscle for determining a myocardial muscle volume; and assigning the second contrast enhanced region to the region representative of the left ventricle absent the myocardial muscle for determining a left ventricle volume.

11. The method of claim 10, wherein said post-processing further comprises:

volume rendering an image of the left ventricle representative of at least one of the myocardial muscle volume or the left ventricle volume at a specified phase of the cardiac cycle.

12. The method of claim 11, wherein said volume rendering comprises:

selecting a cardiac phase and a cardiac region of interest for volume rendering;

acquiring the cardiac volume data for the selected cardiac phase;

reconstructing an image of the cardiac region of interest at the selected cardiac phase in a 3D model; and displaying the reconstructed 3D model image.

13. The method of claim 12, wherein said post-processing further comprises:

determining an image of a phase of the cardiac cycle representative of at least one of end diastole or end systole.

14. The method of claim 13, wherein said determining an image comprises:

applying an EKG as a reference for identifying the time windows in the cardiac cycle representative of end systole and end diastole, the end systole time window being defined by the EKG reading following a first QRS, and the end diastole time window being defined by the EKG reading prior to a second QRS;

determining from the acquired first volume and at least a second volume of cardiac data the image of the phase of the cardiac cycle having the largest left ventricle volume;

determining from the acquired first volume and at least a second volume of cardiac data the image of the phase of the cardiac cycle having the smallest left ventricle volume;

designating the image of the phase of the cardiac cycle having the largest left ventricle volume as end diastole; and designating the image of the phase of the cardiac cycle having the smallest left ventricle volume as end systole.

15. The method of claim 14, wherein said post-processing further comprises:

reconstructing images of the heart at the end diastole and end systole phases; and displaying the reconstructed images.

16. The method of claim 15, wherein said post-processing further comprises:

calculating at least one of end diastole volume, end systole volume, stroke volume, ejection fraction, cardiac output, myocardial muscle wall thickness, left ventricle volume, or motion of the myocardial muscle wall.

17. A method for acquiring and analyzing cardiac data of a patient, comprising:

acquiring a first volume of cardiac data over the course of at least one heart cycle from a single pass of the heart by a medical scanner in the absence of absorbed contrast enhancing media;

processing the first volume of cardiac data for image reconstruction and visualization;

determining an anatomical region of interest from the acquired first volume of cardiac data;

acquiring a series of volumes of cardiac data, representative of at least a subset of the anatomical region of interest, from the medical scanner in the presence of absorbed contrast enhancing media;

processing the series of volumes of cardiac data for image reconstruction and visualization;

reconstructing and visualizing a first and at least a second image set from the acquired first and series of volumes of cardiac data, respectively; and post-processing the series of volumes of cardiac data for visualization and analysis of information relating to perfusion.

18. The method of claim 17, wherein said post-processing comprises:

creating a series of at least one of short-axis reformatted images or volume-rendered 3D images of the heart from the series of volumes of cardiac data;

segmenting an anatomical region of the heart;

partitioning the anatomical region into at least one segment of interest for providing information relating to perfusion defects; and visualizing the degree of perfusion in the anatomical region.

19. The method of claim 18, wherein said segmenting an anatomical region comprises:

segmenting at least one of the myocardium, septum, right ventricle, or left ventricular.

20. The method of claim 18, wherein said visualizing the degree of perfusion comprises:

visualizing enhanced pixels in response to the contrast enhancing media.

21. The method of claim 20, wherein said visualizing enhanced pixels comprises:

visualizing the enhanced pixels in response to the contrast enhancing media in at least one of a grey scale or a color scheme and in at least one of short axis images or long axis images of the heart.

22. The method of claim 21, wherein said post-processing the series of volumes of cardiac data for visualization and analysis further comprises:

visualizing images of enhanced pixels of an anatomical region of interest superimposed on a region of interest of the myocardium.

23. The method of claim 22, further comprising:

visualizing the superimposed images at a selected point in time.

24. The method of claim 23, further comprising:

visualizing the superimposed images at different time points for showing the dynamic changes of perfusion over the time duration involved in acquiring the series of volumes of cardiac data.

25. The method of claim 18, wherein said post-processing further comprises:

calculating a temporal profile of contrast enhancement for a contrast enhanced anatomical region for measuring the time to reach a specified level of enhancement.

26. The method of claim 25, wherein said post-processing further comprising:

displaying the temporal profile.

* * * * *

UNITED STATES PATENT AND TRADEMARK OFFICE
CERTIFICATE OF CORRECTION

PATENT NO. : 6,628,743 B1
DATED : September 30, 2003
INVENTOR(S) : Drummond et al.

It is certified that error appears in the above-identified patent and that said Letters Patent is hereby corrected as shown below:

Drawings,
Figure 4, step 305, delete "cadiac" and insert -- cardiac --.

Column 3,
Line 41, after "system" delete "220" and insert -- 230 --.

Column 12,
Lines 45 and 65, before "of" delete "volumes" and insert -- volume --.

Column 13,
Lines 11, 29 and 48, before "of" delete "volumes" and insert -- volume --.

Signed and Sealed this

Twenty-eighth Day of February, 2006

JON W. DUDAS
*Director of the United States Patent and Trademark Office*